United States Patent [19]
Shutske et al.

[11] Patent Number: 5,869,480
[45] Date of Patent: Feb. 9, 1999

[54] SUBSTITUTED-4-AMINO-3-PYRIDONOLS

[75] Inventors: Gregory Michael Shutske, Flemington; Kevin James Kapples, Little York, both of N.J.; John Dick Tomer, Perkasie, Pa.; Nicholas Joseph Hrib, Somerville; John Gerard Jurcak, Somerset, both of N.J.

[73] Assignee: Hoechst Marion Roussel Inc., Kansas City, Mo.

[21] Appl. No.: 88,928

[22] Filed: Jun. 2, 1998

Related U.S. Application Data

[62] Division of Ser. No. 602,693, Feb. 16, 1996, Pat. No. 5,821,239, which is a continuation of Ser. No. 753,463, Sep. 3, 1991, abandoned, which is a continuation of Ser. No. 589,113, Sep. 27, 1990, abandoned.

[51] Int. Cl.$^6$ .......................... A61K 31/55; C07D 401/12
[52] U.S. Cl. ............................................. 514/212; 540/597
[58] Field of Search ............................... 540/597; 514/212

[56] References Cited

U.S. PATENT DOCUMENTS

| 4,734,275 | 3/1988 | Lalezari et al. | 514/353 |
|---|---|---|---|
| 4,735,958 | 4/1988 | Roth et al. | 514/343 |
| 4,859,663 | 8/1989 | Greve et al. | 514/212 |

FOREIGN PATENT DOCUMENTS

| 0361489 | 4/1990 | European Pat. Off. . |
|---|---|---|
| 0369388 | 5/1990 | European Pat. Off. . |
| 2021113 | 11/1979 | United Kingdom . |

OTHER PUBLICATIONS

Current Neurology, vol. 6, Chapter 11, Appel, Stanley H., pp. 289–324 (1987).
Reed, J.N. et al., Tetrahedron Letters, vol. 24, pp. 3795–3456 (1983).
Marehini et al., J. Org. Chem., vol. 40, pp. 3453–3456 (1975).
Chemical Abstracts, vol. 90, No. 25, Jun. 1979, No. 203170M.
Chemical Abstracts, vol. 110, No. 23, Jun. 5, 1989, No. 205075K.
Arzneimettelforschung–Drug Research, vol. 39, No. 7, Jul. 1989, Aulendorf, DE pp. 762–765.
Gracon, S., Abstract Third International Conference on Alzheimer's Disease and Related Disorders, Jul. 12–17, 1992.
Eagger et al, British Journal of Psychiatry (1992) 160, pp. 36–40.
FDC Reports "The Pink Sheet", Mar. 22, 1993, pp. 7–9.
FDC Reports "The Pink Sheet", Nov. 10, 1992, pp. T&G–2 and 3.
Bellamy et al, Chem. Abst. vol. 90, abstract 203170 (1979).
Berger et al., Chem. Abst. vol. 111, abstract 108504 (1989).

*Primary Examiner*—Richard L. Raymond
*Attorney, Agent, or Firm*—Frommer Lawrence & Haug LLP

[57] ABSTRACT

There are disclosed various substituted 4-amino-3-pyridinol compounds of the formula below,

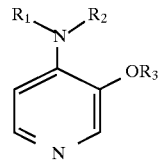

where $R_1$, $R_2$ and $R_3$ are as defined in the specification, which are useful for alleviating various memory dysfunctions characterized by a cholinergic deficit such as Alzheimer's disease.

5 Claims, No Drawings

SUBSTITUTED-4-AMINO-3-PYRIDONOLS

This application is a divisional of application Ser. No. 08/602,693, filed Feb. 16, 1996 now U.S. Pat. No. 5,821,239, which is a continuation of application Ser. No. 07/753,463, filed Sep. 3, 1991, now abandoned, which is a continuation of application Ser. No. 07/589,113, filed Sep. 27, 1990, now abandoned.

The present invention relates to compounds of the formula,

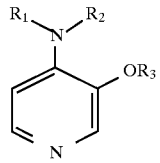
(I)

where $R_1$ is hydrogen or loweralkyl;

$R_2$ is hydrogen, loweralkyl, cycloalkyl, arylloweralkyl, loweralkylcarbonyl or loweralkoxycarbonyl; or alternatively the group

as a whole is

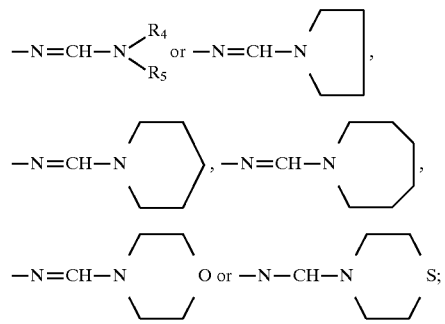

wherein $R_4$ is loweralkyl and $R_5$ is loweralkyl, cycloalkyl or arylloweralkyl; and $R_3$ is hydrogen,

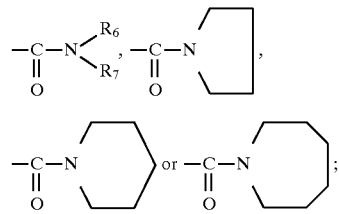

wherein $R_6$ is hydrogen, loweralkyl or phenyl, and $R_7$ is hydrogen or loweralkyl, with the proviso that $R_1$, $R_2$ and $R_3$ may not all be hydrogen, which compounds are useful for alleviating memory dysfunctions characterized by a cholinergic deficit.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term cycloalkyl shall mean a cycloalkyl group of 3 to 7 carbon atoms.

The term halogen shall mean fluorine, chlorine, bromine or iodine.

The term aryl shall mean a phenyl group substituted with 0, 1 or 2 substituents which of each being independently loweralkyl, loweralkoxy, halogen or trifluoromethyl.

Throughout the specification and the appended claims, a given chemical formula or name shall encompass all stereo and tautomeric isomers where such isomers exist.

The compounds of this invention are prepared by utilizing one or more of the synthetic steps described below.

Throughout the description of the synthetic steps, the notations $R_1$ through $R_7$ shall have the respective meanings given above unless otherwise stated or indicated.

STEP A

4-Amino-3-pyridinol is allowed to react with an acetal of Formula IIa or IIb where

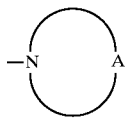

represents

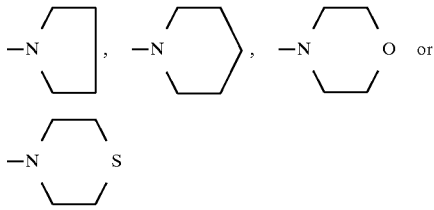

to afford a compound of Formula IIIa or IIIb, respectively. This reaction is typically conducted at a temperature of 25° to 100° C. Optionally, a suitable third chemical may be added to the reaction mixture as a solvent such as toluene.

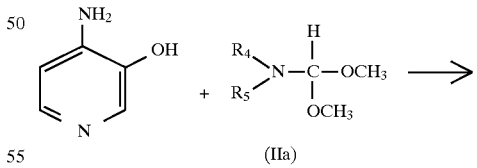
(IIa)

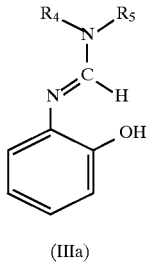
(IIIa)

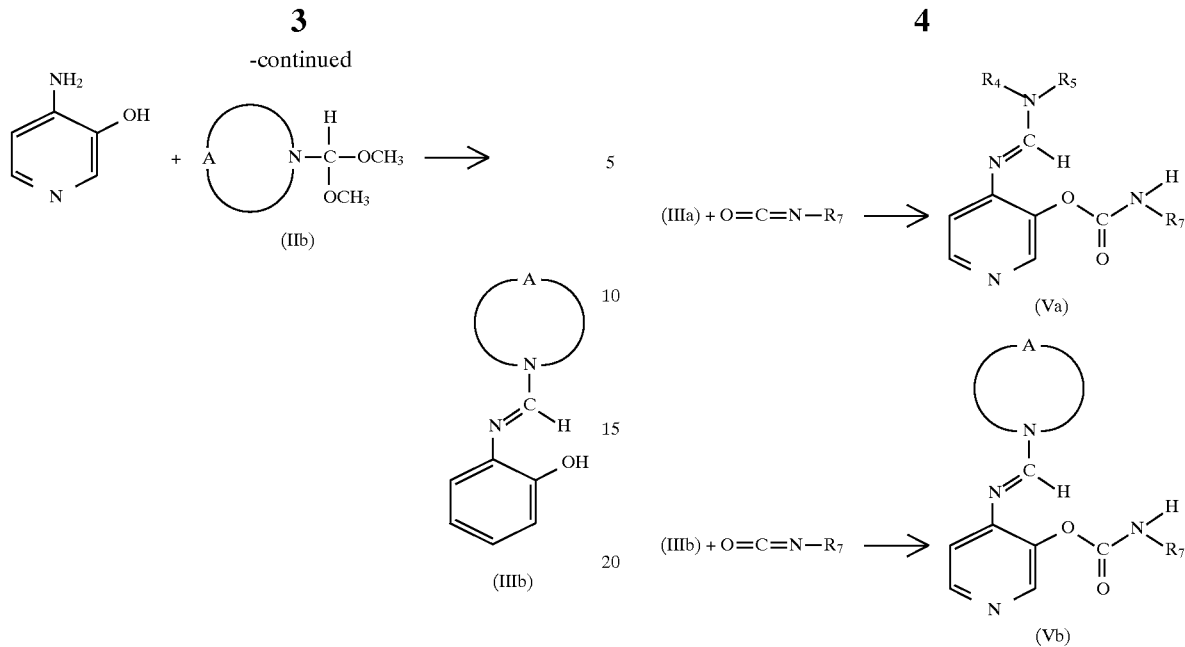

STEP B

Alternatively to the above, a compound of Formula IIIc obtained from STEP A is allowed to react with an amine of Formula IVa or IVb to afford a compound of Formula IIIa or IIIb, respectively. This reaction is typically conducted in a suitable solvent such as toluene at a temperature of 100° to 150° C.

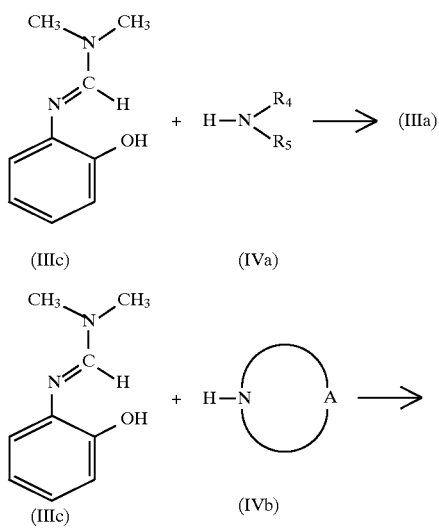

STEP C

Compound IIIa or IIIb is allowed to react with an isocyanate of the formula O=C=N—R₇ in a routine manner known to the art to afford a compound of Formula Va or Vb, respectively.

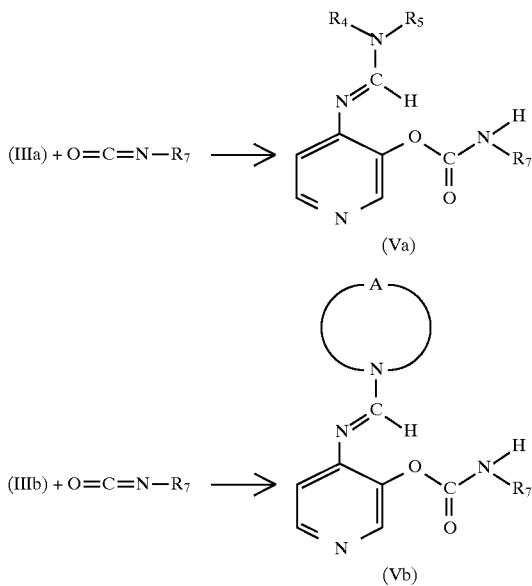

STEP D

Compound IIIa or IIIb is allowed to react with a carbonyl chloride compound of Formula VIa (where $R_6 \neq H$) in a routine manner known to the art to afford a compound of Formula VIIa or VIIb, respectively.

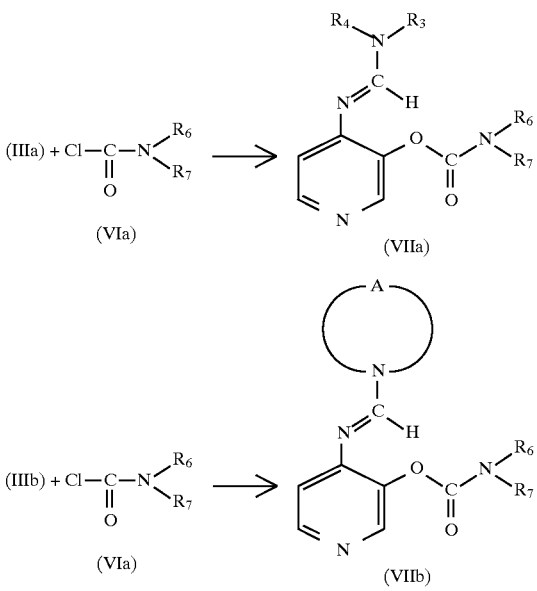

STEP E

Compound IIIa or IIIb is allowed to react with a carbonyl chloride compound of Formula VIII where

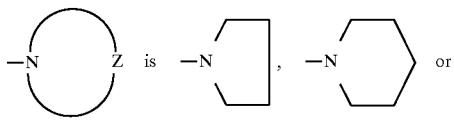

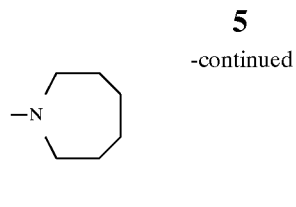

in a routine manner known to the art to afford a compound of Formula IXa or IXb, respectively.

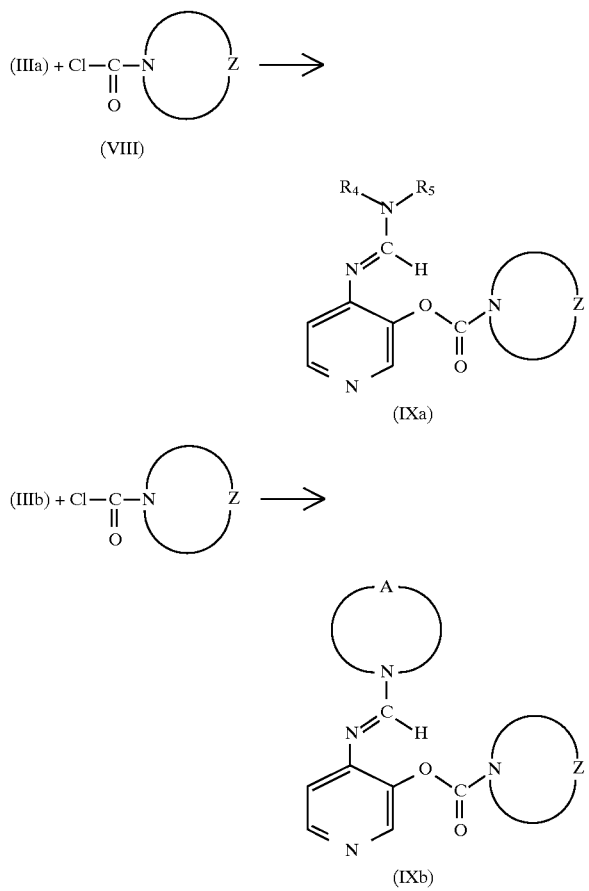

STEP F

Compound VIIa or VIIb is allowed to react with water to afford a compound of Formula Xa. Similarly, compound IXa or IXb is allowed to react with water to afford a compound of Formula Xb. Typically, each hydrolysis reaction is conducted with the aid of a suitable acid such as trifluoroacetic acid at a temperature of 50° to 150° C. For the purpose of this reaction step, it is convenient to use a compound of Formula VIIa or IXa in which $R_4$ and $R_5$ are both methyl.

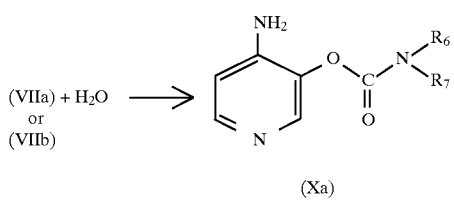

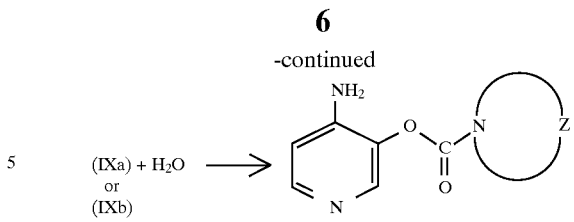

STEP G

As an alternative to the foregoing steps, a compound of Formula XI, where $R_6'$ and $R_7'$ are each independently a loweralkyl of 2 to 6 carbon atoms, is allowed to react with secondary-butyllithium in the presence of tetramethylethylenediamine (TMEDA) to accomplish ortho-lithiation. The resultant lithio compound is first treated with tosyl azide and the resultant product is directly reduced with $NaBH_4$ under a phase transfer condition (tetra-n-butylammonium hydrogen sulfate is conveniently used for this purpose) to afford a compound of Formula Xc. The above reaction procedure is an application of the method described by Reed and Sniekus, Tetrahedron Letters, Volume 24, pp 3795–3798 (1983).

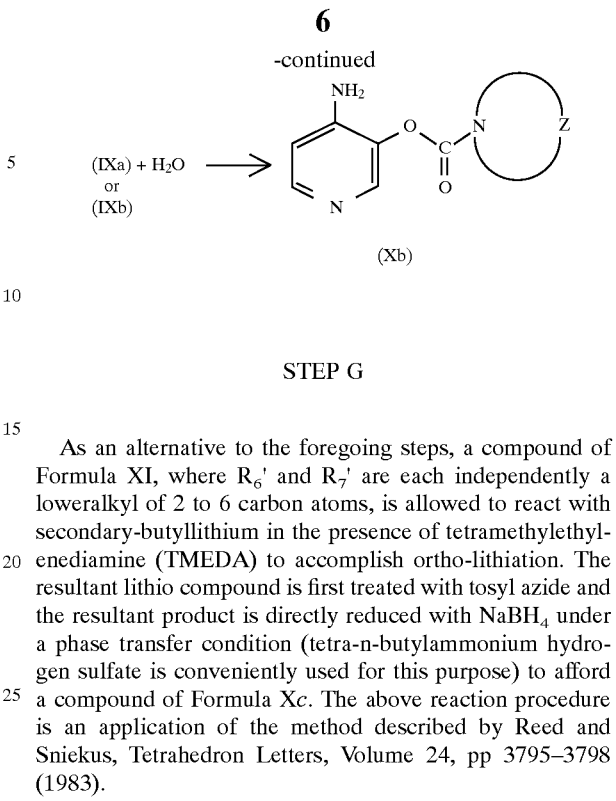

STEP H

A compound of Formula XII (which can be obtained by allowing compound XI to react with secondary-BuLi and thereafter allowing the resultant lithio compound to react with dibromoethane in a routine manner known to the art) is allowed to react with a secondary amine of Formula XIII where $R_1'$ is loweralkyl, and $R_2'$ is loweralkyl, cycloalkyl or arylloweralkyl in the presence of copper (I) chloride to afford a compound of Formaula XIV. This reaction is typically conducted in a suitable solvent such as 1-methyl-2-pyrrolidinone at a temperature of 125° to 200° C.

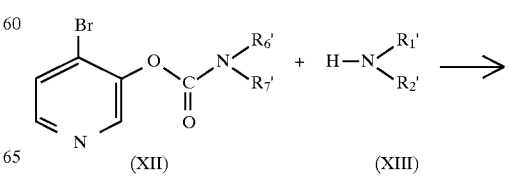

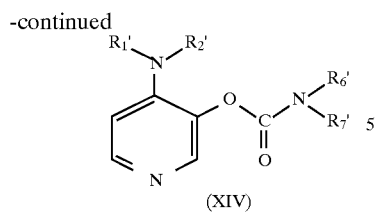

(XIV)

STEP I

As an alternative to STEP D, Compound Xc is allowed to react with Compound IIa or IIb in substantially the same manner as in STEP A to afford a compound of Formula VIIc or VIId, respectively. In other words, this represents a procedure where a methyleneamino group is introduced to the 4-position of the pyridine ring after a carbamate group has been introduced to the 3-position of the pyridine ring, which is in contrast to STEP D where a carbamate group is introduced after a methyleneamino group has been introduced.

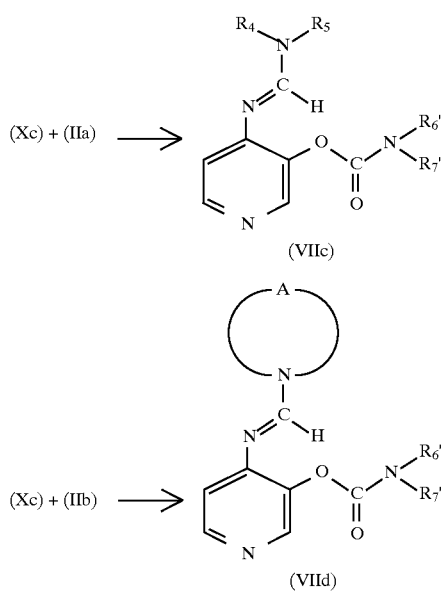

STEP J

Compound Xa or Xb is allowed to react with an acyl chloride of Formula XV where $R_8$ is a loweralkyl group of 1 to 6 carbon atoms in a routine manner known to the art to afford a compound of Formula XVIa or XVIb, respectively.

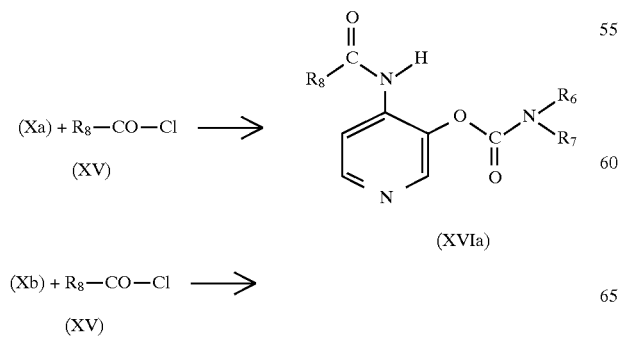

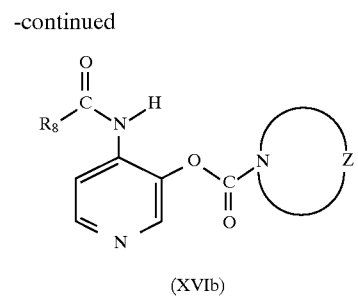

(XVIb)

STEP K

Compound XVIa or XVIb is reduced with the aid of borane/methyl sulfide complex in order to selectively reduce the amide function to afford a compound of Formula XVIIa or XVIIb, respectively. Typically, this reaction is conducted in a suitable solvent such as tetrahydrofuran at a temperature of 0° to 100° C.

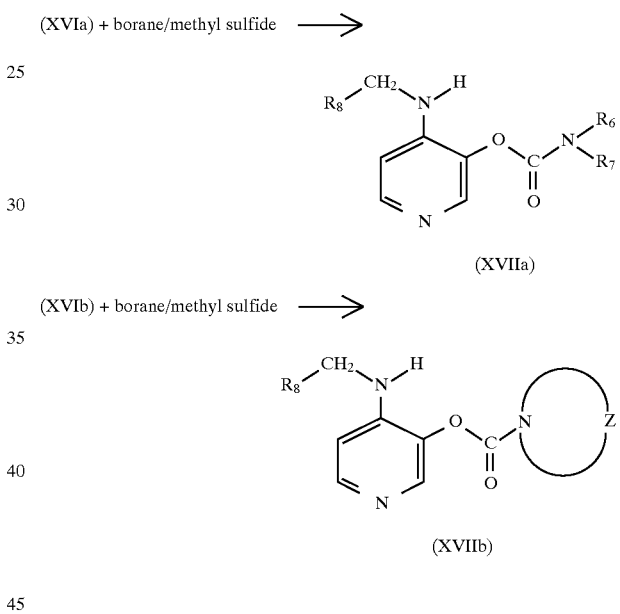

STEP L

Compound Xa or Xb is allowed to react with an aryl aldehyde of the formula $R_9$—CHO where $R_9$ is an aryl group to afford an imine compound of Formula XIXa or XIXb, respectively, and each imine is reduced with $NaBH_4$ in a routine manner known to the art to afford a compound of XXa or XXb, respectively. Typically, the imine formation is conducted in a suitable solvent such as benzene at a temperature of 50° to 125° C.

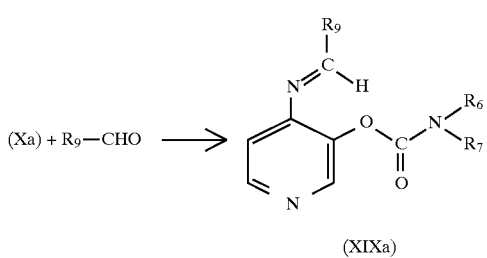

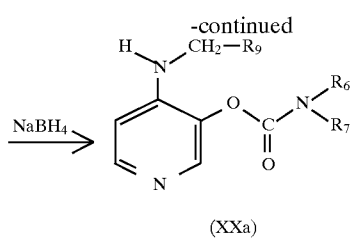

(XXa)

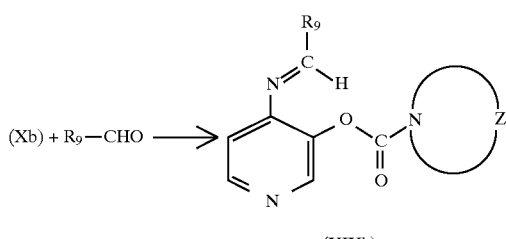

(XIXb)

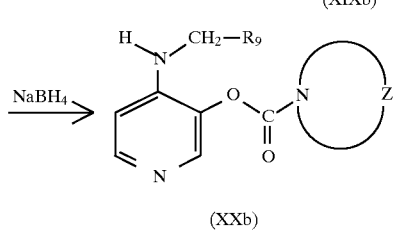

(XXb)

STEP M

Compound X*a* or X*b* is allowed to react with a dicarbonate of Formula XXI where $R_{10}$ is loweralkyl to afford a compound of Formula XXII*a* or XXII*b*, respectively. This reaction is typically conducted in a suitable solvent such as dichloromethane at a temperature of 0° to 50° C.

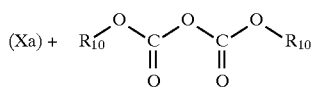

(XXI)

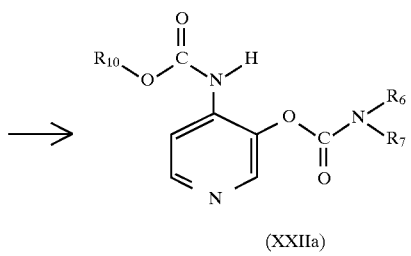

(XXIIa)

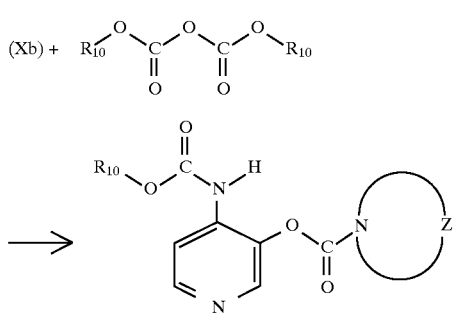

(XXIIb)

STEP N

A carboxylic acid of the formula $R_2''$—COOH where $R_2''$ is a loweralkyl group of 1–5 carbon atoms is treated with $NaBH_4$ typically in a suitable solvent such as benzene and thereafter Compound X*a* or X*b* is added to the reaction mixture to afford a compound of Formula XXIII*a* or XXIII*b*, respectively. The first reaction is typically conducted at a temperature of 0° to 50° C. and the second reaction is typically conducted at a temperature of 50° to 100° C. For details of this synthetic step, the reader is referred to Marchini et al., J. Org. Chem., Volume 40, pp 3453–3456 (1975).

(Xa) + $R_2''$—COOH + $NaBH_4$ →

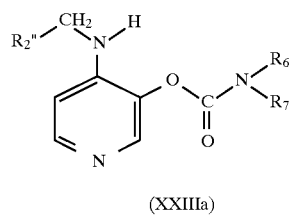

(XXIIIa)

(Xb) + $R_2''$—COOH + $NaBH_4$ →

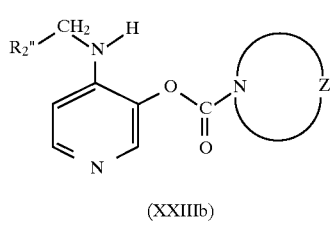

(XXIIIb)

The compounds of Formula I of the present invention are useful for the treatment of various memory dysfunctions characterized by a decreased cholinergic function such as Alzheimer's disease.

This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. We have determined in vitro inhibition of acetylcholinesterase activity in rat striatum.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain roughly correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinominetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying cholinesterase activity. This is a modification of the method of Ellman et al., Biochem. Pharmacol. 7, 88 (1961).

Procedure

A. Reagents
1. 0.05M Phosphate buffer, pH 7.2
    (a) 6.85 g $NaH_2PO_4.H_2O$/100 ml distilled $H_2O$
    (b) 13.40 g $Na_2HPO_4.7H_2O$/100 ml distilled $H_2O$
    (c) add (a) to (b) until pH reaches 7.2
    (d) Dilute 1:10
2. Substrate in buffer
    (a) 198 mg acetylthiocholine chloride (10 mM)
    (b) q.s. to 100 ml with 0.05M phosphate buffer, pH 7.2 (reagent 1)
3. DTNB in buffer
    (a) 19.8 mg 5,5-dithiobisnitrobenzoic acid (DTNB) (0.5 mM)
    (b) q.s. to 100 ml with 0.05M phosphate buffer, pH 7.2 (reagent 1)
4. A 2 mM stock solution of the test drug is made up in a suitable solvent and q.s. to volume with 0.5 mM DTNB (reagent 3).
    Drugs are serially diluted (1:10) such that the final concentration (in cuvette) is $10^{-4}$M and screened for activity. If active, $IC_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 25 microliter aliquot of the homogenate is added to 1.0 milliter vehicle or various concentrations of the test drug and preincubated for 10 minutes at 37° C.

C. Assay

Enzyme activity is measured with the Beckman DU-50 spectrophotometer. This method can be used for $IC_{50}$ determinations and for measuring kinetic constants.

Instrument Settings

Kinetics Soft-Pac Module #598273 (10)
Program #6 Kindata:
Source—Vis
Wavelength—412 nm
Sipper—none
Cuvettes—2 ml cuvettes using auto 6-sampler
Blank—1 for each substrate concentration
Interval time—15 seconds (15 or 30 seconds for kinetics)
Total time—5 minutes (5 or 10 minutes for kinetics)
Plot—yes
Span—autoscale
Slope—increasing
Results—yes (gives slope)
Factor—1
  eb;normal Reagents are added to the blank and sample cuvettes as follows:

Blank: 0.8 ml Phosphate Buffer/DTNB
    0.8 ml Buffer/Substrate
Control: 0.8 ml Phosphate Buffer/DTNB/Enzyme
    0.8 ml Phosphate Buffer/Substrate
Drug: 0.8 ml Phosphate Buffer/DTNB/Drug/Enzyme
    0.8 ml Phosphate Buffer/Substrate Blank values are determined for each run to control for non-enzymatic hydrolysis of substrate and these values are automatically subtracted by the kindata program available on kinetics soft-pac module. This program also calculates the rate of absorbance change for each cuvette.

For $IC_{50}$ Determinations

Substrate concentration is 10 mM diluted 1:2 in assay yielding final concentration of 5 mM. DTNB concentration is 0.5 mM yielding 0.25 mM final concentration.

$$\% \text{ Inhibition} = \frac{\text{slope control} - \text{slope drug}}{\text{slope control}} \times 100$$

$IC_{50}$ values are calculated from log-probit analysis

Results of this assay for some of the compounds of this invention and physostigmine (reference compound) are presented in Table 1.

TABLE 1

| Compound | Inhibitory Concentration ($\mu$M) Brain AChE |
|---|---|
| 4-[[(Dimethylamino)methylene]amino]-3-pyridinol ethylcarbamate | 9.37 |
| 4-[[(Dimethylamino)methylene]amino]-3-pyridinol N,N-dimethylcarbamate | 83.0 |
| 4-Amino-3-pyridinol N,N-dimethylcarbamate trifluoroacetate | 13.4 |
| 4-[[(Dimethylamino)methylene]amino]-3-pyridinol methylcarbamate | 12.6 |
| 4-[[(1-Piperidinyl)methylene]amino]-3-pyridinol N,N-dimethylcarbamate | 47.1 |
| 4-[[(1-Pyrrolidinyl)methylene]amino]-3-pyridinol N,N-dimethylcarbamate | 9.38 |
| Physostigmine | 0.006 |

This utility is further demonstrated by the ability of these compounds to restore cholinergically deficient memory in the Dark Avoidance Assay described below.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for some of the compounds of this invention and those for tacrine and pilocarpine (reference compounds) are presented in Table 2.

TABLE 2

| Compound | Dose (mg/kg of body weight, s.c) | % of Animals with Scopolamine Induced Memory Deficit Reversal |
|---|---|---|
| 4-[[(Dimethylamino)-methylene]amino]-3-pyridinol N,N-diethylcarbamate | 0.3 | 26.6% |
| 4-[[(Dimethylamino)-methylene]amino]-3-pyridinol ethylcarbamate | 0.1 | 20.0% |
|  | 0.3 | 21.4% |
| 4-Amino-3-pyridinol N,N-dimethylcarbamate trifluoroacetate | 0.3 | 26.6% |
| Tacrine | 0.63 | 13% |
| Pilocarpine | 5.0 | 13% |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:

4-[[(dimethylamino)methylene]amino]-3-pyridinol;

4-[[(diethylamino)methylene]amino]-3-pyridinol;

4-[[(diisopropylamino)methylene]amino]-3-pyridinol;

4-[[(1-pyrrolidinyl)methylene]amino]-3-pyridinol;

4-[[(1-piperidinyl)methylene]amino]-3-pyridinol;

4-[[(hexahydro-1H-azepin-1-yl)methylene]amino]-3-pyridinol;

4-[[(4-morpholinyl)methylene]amino]-3-pyridinol;

4-[[(N-methyl-N-butylamino)methylene]amino]-3-pyridinol;

4-[[(N-cyclohexyl-N-methylamino)methylene]amino]-3-pyridinol;

4-[[(4-thiomorpholinyl)methylene]amino]-3-pyridinol;

4-[[(dimethylamino)methylene]amino]-3-pyridinol methylcarbamate;

4-[[(dimethylamino)methylene]amino]-3-pyridinol ethylcarbamate;

4-[[(dimethylamino)methylene]amino]-3-pyridinol N,N-dimethylcarbamate;

4-[[(dimethylamino)methylene]amino]-3-pyridinol phenylcarbamate;

4-[[(dimethylamino)methylene]amino]-3-pyridinol 1-piperidinecarbamate;

4-[[(dimethylamino)methylene]amino]-3-pyrdinol N,N-dimethylcarbamate;

4-[[(dipropylamino)methylene]amino]-3-pyridinol N,N-dimethylcarbamate;

4-[[(1-pyrrolidinyl)methylene]amino]-3-pyridinol N,N-dimethylcarbamate;

4-[[(1-piperidinyl)methylene]amino]-3-pyridinol N,N-dimethylcarbamate;

4-[[(hexahydro-azepin-1-yl)methylene]amino]-3-pyridinol N,N-dimethylcarbamate;

4-[[(4-morpholinyl)methylene]amino]-3-pyridinol N,N-dimethylcarbamate;

4-amino-3-pyridinol N,N-dimethylcarbamate;

4-amino-3-pyridinol 1-piperidinecarbamate;

4-amino-3-pyridinol N,N-diethylcarbamate;

4-dimethylamino-3-pyridinol N,N-diethylcarbamate;

4-[[(dimethylamino)methylene]amino]-3-pyridinol N,N-diethylcarbamate;

4-acetylamino-3-pyridinol N,N-diethylcarbamate;

4-ethylamino-3-pyridinol N,N-diethylcarbamate;

4-benzylamino-3-pyridinol N,N-diethylcarbamate;

4-t-butyloxycarbonylamino-3-pyridinol N,N-diethylcarbamate;

4-propylamino-3-pyridinol N,N-diethylcarbamate;

4-(2-methylpropyl)amino-3-pyridinol N,N-diethylcarbamate;

4-propylamino-3-pyridinol;

4-ethylamino-3-pyridinol;

4-butylamino-3-pyridinol;

4-[[(dihexylamino)methylene]amino]-3-pyridinol N,N-dimethyl-carbamate;

4-[[(diisopropylamino)methylene]amino]-3-pyridinol N,N-dimethylcarbamate;

4-[[(N-methyl-N-butylamino)methylene]amino]-3-pyridinol N,N-dimethylcarbamate;

4-[[(N-methyl-N-cyclohexylamino)methylene]amino]-3-pyridinol N,N-dimethylcarbamate;

4-[[(benzylmethylamino)methylene]amino]-3-pyridinol;

4-[[(N-benzyl-N-methylamino)methylene]amino]-3-pyridinol N,N-dimethylcarbamate; and 4-[[(thiomorpholin-4-yl)methylene]amino]-3-pyridinol N,N-dimethylcarbamate.

EXAMPLE 1

4-[[(Dimethlyamino)methylene]amino]-3-pyridinol

A solution prepared from of 4-amino-3-pyridinol (110g) and 10 ml of N,N-dimethylformamide dimethyl acetal was refluxed for 30 minutes. At the end of this time, the reaction mixture was concentrated under reduced pressure and the residue was passed over a short column of florisil, eluting with 5% methanol/ethyl acetate. The eluate was concentrated and the residue and recrystallized from ethyl acetate/pentane to afford 0.91 g of analytically pure product, m.p. 121°–123°.

ANALYSIS:

Calculated for $C_8H_{11}N_3O$: 58.17% C 6.70% H 25.44% N; Found: 58.07% C 6.68% H 25.37% N

EXAMPLE 2

4-[[(Diethylamino)methylene]amino]-3-pyridinol

A mixture of 4-amino-3-pyridinol (3.90 g), N,N-diethylformamide dimethyl acetal (11.68 g) and toluene (20 mL) was heated under nitrogen for 2 hours. The solution was concentrated under reduced pressure. The resulting liquid was filtered through silica gel with 10% ethanol in tetrahydrofuran to give a solid. Recrystallization of the purified product from ethyl acetate/hexanes afforded 4.21 g of crystalline solid, m.p. 104°–106° C.

ANALYSIS:

Calculated for $C_{10}H_{15}N_3O$: 62.15% C 7.82% H 21.74% N; Found: 62.47% C 7.92% H 21.87% N

EXAMPLE 3

4-[[(Diisopropylamino)methylene]amino]-3-pyridinol

A mixture of 4-amino-3-pyridinol (3.0 g), N,N-diisopropylformamide dimethyl acetal (9.54 g) and 15 ml dry toluene was stirred at room temperature for 18 hours and thereafter heated to 60°–70° C. After 90 minutes, the mixture was cooled to room temperature, concentrated in vacuo and chromatographed on silica using 10:90 $CH_3OH$/ethyl acetate as an eluent. The fractions containing the desired product were combined and concentrated to a thick oil, which solidified on refrigeration. This solid (5.3 g) was triturated with hexane three times to provide the product as a white solid, m.p. 77°–79° C.

ANALYSIS:

Calculated for $C_{12}H_{19}N_3O$: 65.13% C 8.65% H 18.99% N; Found: 65.17% C 8.65% H 19.02% N

EXAMPLE 4

4-[[(1-Pyrrolidinyl)methylene]amino]-3-pyridinol dihydrochloride

4-Amino-3-pyridinol (2.5 g) was added to 1-pyrrolidinylformamide dimethyl acetal[1] (20 ml), and the mixture was stirred at room temperature for a half hour and concentrated under high vacuum at 40°–50° C. The oily residue was triturated twice from diethyl ether and recrystallized from ethyl acetate/diethyl ether to yield 2.76 g of solid. The solid was dissolved in a mixture of ethyl acetate (90 ml) and methanol (10 ml), the mixture was filtered to remove insolubles, and ethereal hydrogen chloride (50 ml) was added to the solution, whereupon 3.62 g of solid was obtained. This was recrystallized from methanol/diethyl ether and dried under high vacuum overnight to yield 2.16 g of product, m.p. 190° C. (dec.).

[1]Hoffmann et al., U.S. Pat. No. 3,949.022.

ANALYSIS:

Calculated for $C_{10}H_{15}Cl_2N_3O$: 45.47% C 5.72% H 15.91% N; Found: 45.05% C 5.88% H 15.73% N

EXAMPLE 5

4-[[(1-Piperidinyl)methylene]amino]-3-pyridinol

4-Amino-3-pyridinol (3.3 g) was added to 1-piperidinylformamide dimethyl acetal (50 ml) and the mixture was stirred at 100° C. until it became homogeneous (approximately one minute). The reaction mixture was cooled, and placed in an ice bath for a half hour. The crystallized product was filtered, washed well with diethyl ether, and air dried to yield 4.64 g of product. This was recrystallized from ethyl acetate and dried under high vacuum and refluxing ethanol overnight to yield 3.39 g of fluffy needles, m.p. 171°–172.5° C.

ANALYSIS:

Calculated for $C_{11}H_{15}N_3O$: 64.37% C 7.37% H 20.47% N; Found: 64.21% C 7.33% H 20.30% N

EXAMPLE 6

4-[[(Hexahydro-1H-azepin-1-yl)methylene]amino]-3-pyridinol

4-Amino-3-pyridinol (6.0 g) was added to N-(hexahydro-1H-azepin-1-yl)-formamide dimethyl acetal (60 ml) and the mixture was stirred at room temperature for a half hour, placed in a 60° C. oil bath and concentrated under high vacuum. The resulting oil was boiled in diethyl etherlpentane (1:1) (300 ml), and the solution was decanted, leaving behind a dark red residue. The solution was concentrated to 100 ml and cooled in an ice bath, and after addition of a few seed crystals, it was placed in a refrigerator overnight to yield 2.66 g of crystalline solid, m.p. 117°–118° C.
ANALYSIS:
Calculated for $C_{12}H_{17}N_3O$: 65.73% C 7.81% H 19.16% N; Found: 65.66% C 7.56% H 18.98% N

EXAMPLE 7

4-[[(4-Morpholinyl)methylene]amino]-3-pyridinol

4-Amino-3-pyridinol (3.5 g) was added to 4-morpholinylformamide dimethyl acetal (50 ml) and the mixture was stirred at 100° C. until it became homogeneous (approximately 3 minutes). The reaction mixture was cooled and placed in an ice bath for a half hour. The crystallized product was filtered, washed well with diethyl ether, and air dried to yield 5.14 g of product. This was recrystallized from methanol and dried under high vacuum and refluxing ethanol overnight to yield 3.89 g of crystals, m.p. 192°–193° C.
ANALYSIS:
Calculated for $C_{10}H_{13}N_3O_2$: 57.96% C 6.32% H 20.28% N; Found: 57.96% C 6.25% H 20.28% N

EXAMPLE 8

4-[[(N-methyl-N-butylamino)methylene]amino]-3-pyridinol

A mixture of 4-[[(dimethylamino)methylene]amino]-3-pyridinol (7.50 g), N-methylbutylamine (8.10 g), ammonium sulfate (0.600 g), and anhydrous toluene (25 mL) was heated at reflux under nitrogen for 2.25 hours. The solution was concentrated under reduced pressure and the crude product chromatographed on silica gel (10% methanol in dichloromethane) to afford 6.04 g of solid. Recrystallization from ethyl acetate/hexanes afforded 3.90 g of a crystalline material, m.p. 83°–85° C.
ANALYSIS:
Calculated for $C_{11}H_{17}N_3O$: 63.74% C 8.27% H 20.27% N; Found: 63.80% C 8.40% H 20.25% N

EXAMPLE 9

4-[[(N-cyclohexyl-N-methylamino)methylene]amino]-3-pyridinol

A mixture of 4-[[(dimethylamino)methylene]amino]-3-pyridinol (5.00 g), N-methylcyclohexylamine (5.20 g), and anhydrous toluene (50 mL) was heated at reflux under nitrogen for 17 hours. The solution was concentrated under reduced pressure and the crude product chromatographed on silica gel (10% methanol in dichloromethane) to afford 5.92 g of solid. Recrystallization from ethyl acetate/hexanes afforded 4.90 g of crystalline material, m.p. 127°–129° C.
ANALYSIS:
Calculated for $C_{13}H_{19}N_3O$: 66.92% C 8.21% H 18.01% N; Found: 66.69% C 7.91% H 17.89% N

EXAMPLE 10

4-[[(4-Thiomorpholinyl)methylene]amino]-3-pyridinol

A mixture prepared from 4-[[(dimethylamino)methylene]amino]-3-pyridinol (5.14 g), thiomorpholine (10.5 ml, distilled from $CaH_2$) and dry toluene (120 ml) was refluxed overnight. The reaction mixture was concentrated, triturated with diethyl ether, adhered to silica (methanol), flash chromatographed (10% methanol/ethyl acetate), and triturated with diethyl ether to yield 6.06 g of product. A 3.5 g sample was recrystallized from methanol, and dried under high vacuum and refluxing isopropanol to yield 2.13 g of crystals, m.p. 197°–198.5° C.
ANALYSIS:
Calculated for $C_{10}H_{13}N_3OS$: 53.79% C 5.87% H 18.82% N; Found: 53.75% C 5.84% H 18.69% N

EXAMPLE 11

4-[[(Dimethylamino)methylene]amino]-3-pyridinol methylcarbamate

To a hot suspension of 4-[[(dimethylamino)methylene]amino]-3-pyridinol (7.0 g) in dry tetrahydrofuran (THF) were added sodium hydride (168 mg) and methyl isocyanate (2.6 ml). The reaction mixture was stirred at room temperature overnight, cooled in an ice-methanol bath and filtered. The solid was washed with diethyl ether and distributed between methylene chloride (250 ml) and saturated ammonium chloride (30 ml) and, extracted twice more with methylene chloride (200 ml). The solution was dried ($MgSO_4$) and concentrated and the solid was recrystallized from ethyl acetate and dried under high vacuum and refluxing ethanol to yield 6.18 g of crystals, m.p. 137°–139° C.
ANALYSIS:
Calculated for $C_{10}H_{14}N_4O_2$: 54.04% C 6.35% H 25.21% N; Found: 53.90% C 6.21% H 25.10% N

EXAMPLE 12

4-[[(Dimethylamino)methylene]amino]-3-pyridinol ethylcarbamate

To a warm solution of 4-[[(dimethylamino)methylene]amino]-3-pyridinol (7.12 g) in dry tetrahydrofuran (150 mL) were added sodium hydride (173 mg) and ethyl isocyanate (3.59 mL). The reaction mixture was stirred at room temperature overnight, cooled in an ice bath and filtered, and the solid was washed with diethyl ether. The solid was distributed between methylene chloride (250 mL) and saturated ammonium chloride (30 mL) and extracted twice more with methylene chloride (100 mL). The solution was dried ($MgSO_4$) and concentrated, and the solid was recrystallized from ethyl acetate to yield 5.7 g of needles, m.p. 138° C. (dec.).
ANALYSIS:
Calculated for $C_{11}H_{16}N_4O_2$: 55.92% C 6.83% H 23.71% N; Found: 55.93% C 6.95% H 23.74% N

EXAMPLE 13

4-[[(Dimethylamino)methylene]amino]-3-pyridinol N,N-dimethylcarbamate

4-[[(Dimethylamino)methylene]amino]-3-pyridinol (1.65 g) was refluxed for 1 hour in 20 ml of benzene containing 1.10 g of $Et_3N$ and 1.10 g of N,N-dimethylcarbamyl chloride. At the end of this time, the reaction mixture was applied directly to a silica column and eluted with 5% $Et_3N$/ethyl acetate. Concentration of the product-containing fractions gave 2.05 g of chromatographically pure product which was distilled in a bulb to bulb apparatus (oven temperature=175° C.) to give analytically pure material, m.p. 64°–66° C.
ANALYSIS:

Calculated for $C_{11}H_{16}N_4O_2$: 55.91% C 6.83% H 23.71% N; Found: 55.63% C 6.76% H 23.51% N

EXAMPLE 14

4-[[(Dimethylamino)methylene]amino]-3-pyridinol phenylcarbamate

To a warm solution of 4-[[(dimethylamino)methylene] amino]-3-pyridinol (3.0 g) in dry tetrahydrofuran (60 mL) was added phenyl isocyanate (2.05 mL). The reaction mixture was stirred at room temperature for 1.5 hours and filtered. The solid was washed with dry diethyl ether, air dried, and dried under high vacuum and refluxing ethanol for 4 hours to yield 4.19 g of solid, m.p. 151 °C.

ANALYSIS:
Calculated for $C_{15}H_{16}N_4O_2$: 63.37% C 5.67% H 19.71% N; Found: 63.13% C 5.79% H 19.60% N

EXAMPLE 15

4-[[(Dimethylamino)methylene]amino]-3-pyridinol 1-piperidinecarbamate

A mixture prepared from 4-[[(dimethylamino)methylene] amino]-3-pyridinol (5.2 g), triethylamine (4.8 mL), piperidine carbonyl chloride (4.89 mL) and benzene (173 mL) was refluxed for a half hour, cooled, poured directly onto a silica column and eluted with 5% Et₃N/ethyl acetate to yield 7.55 g of product. Recrystallization from ethyl acetate and drying under high vacuum for 2 hours yielded 5.5 g of crystals, m.p. 90°–91 °C.

ANALYSIS:
Calculated for $C_{14}H_{20}N_4O_2$: 60.85% C 7.30% H 20.27% N; Found: 60.78% C 7.45% H 20.17% N

EXAMPLE 16

4-[[(Diethylamino)methylene]amino]-3-pyridinol N,N-dimethyl carbamate

To a solution prepared from 4-[[(diethylamino) methylene]amino]-3-pyridinol (3.12 g), triethylamine (3.34 g) and tetrahydrofuran (50 mL) was added N,N-dimethylcarbamyl chloride (2.28 g) under nitrogen. The resulting mixture was stirred at ambient temperature for 6 hours, diluted with ether (50 mL) and filtered. The filtrate was concentrated under reduced pressure and the residue chromatographed on silica gel (elution with 10% methanol in dichloromethane) to give 3.00 g of solid. Recrystallization from ether/hexanes afforded 1.57 g of crystalline solid, m.p. 73°–74° C.

ANALYSIS:
Calculated for $C_{13}H_{20}N_4O_2$: 59.07% C 7.63% H 21.20% N; Found: 59.06% C 7.82% H 21.16% N

EXAMPLE 17

4-[[(Dipropylamino)methylene]amino]-3-pyridinol N,N-dimethylcarbamate

A mixture prepared from 4-[[(dipropylamino)methylene] amino]-3-pyridinol (3.22 g), triethylamine (3.15 g), dimethylcarbamyl chloride (2.01 mL) and tetrahydrofuran (100 mL) was refluxed for 1 hour, cooled, poured directly onto a silica column and eluted successively with ethyl acetate and 5% Et₃N/ethyl acetate. The eluate was concentrated and the solid was recrystallized from diethyl ether to yield 2.99 g of product, m.p. 84°–85° C.

ANALYSIS:
Calculated for $C_{15}H_{24}N_4O_2$: 61.62% C 8.27% H 19.16% N; Found: 61.74% C 8.33% H 19.23% N

EXAMPLE 18

4-[[(1-Pyrrolidinyl)methylene]amino]-3-pyridinol N,N-dimethylcarbamate

A mixture prepared from 4-[[(1-pyrrolidinyl)methylene] amino]-3-pyridinol (3.79 g), triethylamine (4.29 mL), dimethylcarbamyl chloride (2.74 mL) and tetrahydrofuran (130 mL) was refluxed for 1 hour, cooled, poured directly onto a silica column and eluted successively with ethyl acetate and 5% Et₃N/ethyl acetate. Recrystallization from ethyl acetate and drying under high vacuum and refluxing acetone for 4 hours yielded 3.55 g of crystals, m.p. 99°–100° C.

ANALYSIS:
Calculated for $C_{13}H_{18}N_4O_2$: 59.53% C 6.92% H 21.36% N; Found: 59.70% C 6.99% H 21.26% N

EXAMPLE 19

4-[[(1-Piperidinyl)methylene]amino]-3-pyridinol N,N-dimethylcarbamate

A mixture prepared from 4-[[(1-piperidinyl)methylene] amino]-3-pyridinol (3.5 g), triethylamine (3.69 mL), dimethylcarbamyl chloride (2.3 mL) and tetrahydrofuran (130 mL) was refluxed for 2 hours, filtered, poured directly onto a silica column and eluted successively with ethyl acetate and 5% Et₃N/ethyl acetate to yield 4.49 g of product. Recrystallization from ethyl acetate and drying under high vacuum yielded 3.94 g of crystals, m.p. 88°–89° C.

ANALYSIS:
Calculated for $C_{14}H_{20}N_4O_2$: 60.85% C 7.30% H 20.27% N; Found: 60.90% C 7.44% H 20.13% N

EXAMPLE 20

4-[[(Hexahydro-azepin-1-yl)methylene]amino]-3-pyridinol N,N-dimethylcarbamate A mixture prepared from 4-[[(hexahydro-azepin-1-yl) methylene]amino]-3-pyridinol (2.9 g), triethylamine (2.86 ml), dimethylcarbamyl chloride (1.83 ml) and tetrahydrofuran (85 ml) was refluxed for 1 hour, cooled, poured directly onto a silica column and eluted successively with ethyl acetate and 5% Et₃N/ethyl acetate. The eluate was concentrated and dried under high vacuum to obtain 3.88 g of oil. The oil solidified in a refrigerator over the weekend, and was triturated with cold pentane to yield 3.31 g of solid, m.p. 68°–70° C.

ANALYSIS:
Calculated for $C_{15}H_{22}N_4O_2$: 62.05% C 7.64% H 19.30% N; Found: 61.86% C 7.55% H 19.20% N

EXAMPLE 21

4-[[(4-Morpholinyl)methylene]amino]-3-pyridinol N,N-dimethylcarbamate

A mixture prepared from 4-[[(4-morpholinyl)methylene] amino]-3-pyridinol (3.04 g), triethylamine (3.19 mL), dimethylcarbamyl chloride (2.04 mL) and tetrahydrofuran (121 mL) was refluxed for 1 hour, cooled, poured directly onto a silica column and eluted successively with ethyl acetate and 5% Et₃N/ethyl acetate. Recrystallization from ethyl acetate (50 mL) and drying under high vacuum and refluxing acetone overnight yielded 3.04 g of fluffy needles, m.p. 127°–129° C.

ANALYSIS:
Calculated for $C_{13}H_{18}N_4O_3$: 56.10% C 6.52% H 20.13% N; Found: 56.10% C 6.84% H 20.16% N

EXAMPLE 22

4-Amino-3-pyridinol N,N-dimethylcarbamate trifluoroacetate

A mixture prepared from 4-[[(dimethylamino)methylene]amino]-3-pyridinol N,N-dimethylcarbamate (7.4 g), trifluoroacetic acid (30 mL) and water (15 mL) was refluxed for a half hour. The reaction mixture was concentrated, filtered over a pad of basic alumina ($CH_2Cl_2$, 30% ethyl acetate/$CH_2Cl_2$, ethyl acetate), recrystallized from methano/diethyl ether, and dried under high vacuum and refluxing ethanol to yield 4.97 g of microcrystals, m.p. 159°–160° C.
ANALYSIS:
Calculated for $C_{10}H_{12}N_3O_4F_3$: 40.69% C 4.10% H 14.23% N; Found: 40.63% C 3.76% H 14.21% N

EXAMPLE 23

4-Amino-3-pyridinol 1-piperidinecarbamate

A mixture prepared from 4-[[(dimethylamino)methylene]amino]-3-pyridinol 1-piperdine carboxylate (3.4 g), trifluoroacetic acid (11 mL) and water (6 mL) was refluxed for a half hour. The reaction mixture was concentrated, dissolved in saturated $NaHCO_3$ (50 mL) and extracted three times with ethyl acetate (450 mL). The extract was dried ($MgSO_4$), concentrated, and triturated with diethyl ether/pentane (1:2) to yield 2.27 g of solid. This was recrystallized from ethyl acetate and dried under high vacuum and refluxing acetone for 4 hours to yield 1.58 g of crystals, m.p. 134° C. (dec.).
ANALYSIS:
Calculated for $C_{11}H_{15}N_3O_2$: 59.71% C 6.83% H 18.99% N; Found: 59.46% C 6.93% H 18.89% N

EXAMPLE 24

4-Amino-3-pyridinol N,N-diethylcarbamate

The N,N-diethylcarbamate of 3-hydroxypyridine (9.70 g) and tetramethylethylenediamine (TMEDA) (6.39 g) were dissolved in 100 mL of dry tetrahydrofuran and the solution was chilled in a dry ice/acetone bath. s-Butyllithium (42 mL of 1.3M solution in cyclohexane) was then added dropwise and the reaction mixture was stirred in the cold bath for 1 hour. At the end of this time, tosyl azide (10.80 g) was added and the reaction mixture was allowed to come to room temperature. Tetra-n-butylammoniumhydrogen sulfate (2.55 g) was then added, followed by the dropwise addition of $NaBH_4$ (5.85 g) in 15 mL of water (rate of addition adjusted in order to control foaming). The resulting mixture was stirred 30 minutes at room temperature and then aqueous HCl was added until the reaction mixture tested acidic to a pH paper. After stirring an additional 30 minutes, the reaction mixture was filtered, made basic with aqueous NaOH, and extracted with ethyl acetate. Drying and concentration gave a residue which was purified by flash chromatography (5% $Et_3N$/ethyl acetate). Concentration of the product-containing fractions afforded 6.75 g of solid. An analytically pure material was obtained by recrystallizatin from ethyl acetate/pentane, m.p. 138°–140° C.
ANALYSIS:
Calculated for $C_{10}H_{15}N_3O_2$: 57.40% C 7.22% H 20.08% N; Found: 57.15% C 7.19% H 19.84% N

EXAMPLE 25

4-Dimethylamino-3-pyridinol N,N-diethylcarbamate, fumarate

A mixture prepared from 4-bromo-3-pyridinol N,N-diethylcarbamate (5.7 g)*, dimethylamine hydrochloride (2.13 g), copper(I) chloride (50 mg) and 1-methyl-2-pyrrolidinone (100 ml) was heated at 170° C. for 6 hours. The reaction mixture was then poured into a dilute $K_2CO_3$ solution and the aqueous phase was extracted with ethyl acetate (3×). The combined organics were washed successively with water and saturated NaCl solution and dried ($MgSO_4$). This was filtered and concentrated to give 3.88 g of oil.

Miah and Snieckus, J. Org. Chem., 50, 5436 (1985).

The compound was dissolved in methanol and treated with 1.1 equivalents of fumaric acid, and thereafter a solid was crystallized out of the solution by addition of ethyl ether. Collection of the solid gave 2.96 g of analytically pure material, m.p. 144°–145° C.
ANALYSIS:
Calculated for $C_{12}H_{19}N_3O_2 \cdot C_4H_4O_4$: 54.38% C 6.56% H 11.89% N; Found: 54.63% C 6.48% H 11.86% N

EXAMPLE 26

4-[[(Dimethylamino)methylene]amino]-3-pyridinol N,N-diethylcarbamate

4-Amino-3-pyridinol N,N-diethylcarbamate (5.80 g) was refluxed for 30 minutes in 50 mL of N,N-dimethylformamide dimethyl acetal. At the end of this time the reaction mixture was concentrated under reduced pressure and the residue was purified by flash chromatography (5% $Et_3N$/ethyl acetate) to give, after concentration of the product-containing fractions, 4.63 g of chromatographically pure product. An analytically pure material was obtained by recrystallizatin from $Et_2O$, m.p. 67°–69° C.
ANALYSIS:
Calculated for $C_{13}H_{20}N_4O_2$ 59.07% C 7.62% H 21.20% N; Found: 59.27% C 7.50% H 21.25% N

EXAMPLE 27

4-Acetylamino-3-pyridinol N,N-diethylcarbamate

4-Amino-3-pyridinol N,N-diethylcarbamate (4.18 g) was dissolved in $CH_2Cl_2$ (75 mL) containing $Et_3N$ (2.22 g). The reaction mixture was chilled in an ice-water bath and then acetyl chloride (1.57 g) was added dropwise. After stirring in the cold bath for 15 minutes, the mixture was concentrated under reduced pressure to a volume of ca. 20 mL. This suspension was applied directly to a flash chromatography column and eluted with 5% $Et_3N$/ethyl acetate. The product-containing fractions were concentrated to give 3.76 g of chromatographically pure product. An analytically pure material was obtained by recrystallization from ethyl acetate/pentane, m.p. 102°–104° C.
ANALYSIS:
Calculated for $C_{12}H_{17}N_3O_3$: 57.36% C 6.82% H 16.72% N; Found: 57.35% C 7.36% H 16.68% N

EXAMPLE 28

4-Ethylamino-3-pyridinol N,N-diethylcarbamate

4-Acetylamino-3-pyridinol N,N-diethylcarbamate (3.43 g) was dissolved in tetrahydrofuran (75 mL) and then the reaction mixture was chilled in an ice-water bath. Borane/methyl sulfide (BMS) was added (3.25 mL, 2.60 g) and the reaction mixture was stirred in the cold bath for 30 minutes. At the end of this time an additional 3.0 mL of BMS was added and stirring was continued for 3 hours. The reaction mixture was then poured into ice/conc. HCl, stirred for 30 minutes, basified with $NH_3$/water and then extracted with ethyl acetate. The organic phase was then dried, concentrated and purified by flash chromatography to give 0.86 g of chromatographically pure product. This product was combined with a crop obtained from another run and recrystallized from hexane to give an analytically pure material, m.p. 107°–108° C.
ANALYSIS:
Calculated for $C_{12}H_{19}N_3O_2$: 60.74% C 8.07% H 17.71% N; Found 60.79% C 8.13% H 17.71% N

EXAMPLE 29

4-Benzylamino-3-pyridinol N,N-diethylcarbamate

4-Amino-3-pyridinol N,N-diethylcarbamate (2.09 g) was refluxed overnight in 100 mL of benzene containing benzaldehyde (1.50 g) and $Et_3N$ (2.0 g). At the end of this time the reaction mixture was concentrated under reduced pressure and the residue was purified by flash chromatography to give, after concentration of the product-containing fractions, 1.91 g of chromatographically pure product. This was combined with the product of another run (total 4.20 g) and dissolved in MeOH (50 mL). $NaBH_4$ (0.37 g) was added in portions and after 30 minutes the reaction mixture was distributed between water and ethyl acetate. The organic phase was dried, concentrated and purified by flash chromatography. The product-containing fractions were concentrated and the residue was recrystallized from ethyl acetate to give 1.85 g of analytically pure product, m.p. 71°–73° C.
ANALYSIS:
Calculated for $C_{17}H_{21}N_3O_2$: 68.21% C 7.07% H 14.04% N; Found: 68.31% C 7.21% H 14.04% N

EXAMPLE 30

4-t-Butyloxycarbonylamino-3-pyridinol N,N-diethylcarbamate

4-Amino-3-pyridinol N,N-diethylcarbamate (2.09 g) was dissolved in $CH_2Cl_2$ (20 mL) and then di-t-butyl dicarbonate (2.20 g) was added in several portions. After stirring for 15 minutes, the mixture was applied directly to a flash chromatography column and eluted with 50% ethyl acetate/$CH_2Cl_2$. The product-containing fractions were concentrated to give 2.89 g of chromatographically pure product. An analytically pure material was obtained by recrystallization from hexane (2.20 g), m.p. 91°–93° C.
ANALYSIS:
Calculated for $C_{15}H_{23}N_3O_4$: 58.24% C 7.49% H 13.58% N; Found: 58.47% C 7.59% H 13.58% N

EXAMPLE 31

4-Propylamino-3-pyridinol N,N-diethylcarbamate

A solution of propionic acid (58.5 ml) in 100 ml of benzene was treated with $NaBH_4$ (9.6 g added portionwise). After the frothing subsided, 4-amino-3-pyridinol N,N-diethylcarbamate (5.30 g) was added and the mixture was heated at 80° C. for 2 hours. The reaction mixture was poured into a dilute NaOH solution and the aqueous phase was extracted with ethyl acetate (3×). The combined organics were washed with water and dried (saturated NaCl, $MgSO_4$). The desired amine was purified via flash chromatography to give 3.2 g of solid, m.p. 60°–70° C. This product was combined with a crop obtained from another run and recrystallized from hexane to give analytically pure material, m.p. 75°–78° C.
ANALYSIS:
Calculated for $C_{13}H_{21}N_3O_2$: 62.12% C 8.42% H 16.72% N; Found: 62.34% C 8.48% H 16.77% N

EXAMPLE 32

4-((2-Methylpropyl)amino)-3-pyridinol N,N-diethylcarbamate

A solution of isobutyric acid (49.85 g) in 100 ml of benzene was treated with $NaBH_4$ (6.91 g added portionwise). After the frothing subsided, 4-amino-3-pyridinol N,N-diethylcarbamate (4.90 g) was added and the mixture was heated at 85° C. for 3 hours. The reaction mixture was poured into a dilute NaOH solution and the aqueous phase was extracted with ethyl acetate (3×). The combined organics were washed with water and dried (saturated NaCl, $MgSO_4$). The desired amine was purified via flash chromatography to give 2.05 g of solid. This product was recrystallized from hexane to give analytically pure material, m.p. 71°–75° C.
ANALYSIS:
Calculated for $C_{14}H_{23}N_3O_2$: 63.37% C 8.74% H 15.87% N; Found: 63.08% C 8.70% H 15.72% N

EXAMPLE 33

4-Propylamino-3-pyridinol hydrochloride

A mixture prepared from 4-propylamino-3-pyridinol N,N-diethylcarbamate (7.3 g) and hydrazine (20 ml) was heated at 80° C. for 3 hours. The reaction mixture was then chilled in ice and the hydrazine was quenched with excess acetone. Concentration in vacuo and purification of the resulting oil via flash chromatography gave 3.3 g of oil. This oil was dissolved in methanol and treated with an ethereal HCl solution to give 2.00 g of powder, m.p. 167°–170° C.
ANALYSIS:
Calculated for $C_8H_{12}N_2O·HCl$: 50.93% C 6.95% H 14.85% N; Found: 50.63% C 7.00% H 15.12% N

EXAMPLE 34

4-Ethylamino-3-pyridinol hydrochloride

4-Acetylamino-3-pyridinol N,N-diethylcarbamate (7.50 g) was dissolved in 60 ml of dry THF and 2.0M $BH_3/(CH_3)_2S$ (40 ml) was added. The reaction mixture was refluxed for 30 minutes and then 10 ml of MeOH was added. After the reaction with the residual diborane had subsided, the solvents were removed under reduced pressure and the residue was re-dissolved in 50 ml of MeOH. This solution was made strongly acidic with $HCl/Et_2O$ and then refluxed for 1 hour. At the end of this time, the solvents were again removed under reduced pressure and anhydrous hydrazine (25 ml) was added. This mixture was warmed at 80° C. for 30 minutes and then concentrated under reduced pressure, giving a residue which was purified by flash chromatography (5% $Et_3N$/EtOAc, then 20% MeOH/$CH_2Cl_2$). After the product-containing fractions were concentrated, the free base was taken up in a minimum of EtOH and the hydrochloride was formed with $HCl/Et_2O$. Recrystallization from EtOH/$Et_2O$ gave 2.31 g of analytically pure material, m.p. 168°–169° C.
ANALYSIS:
Calculated for $C_7H_{10}N_2O·HCl$: 48.15% C 6.35% H 16.04% N; Found: 48.15% C 6.34% H 15.90% N

EXAMPLE 35

4-Butylamino-3-pyridinol hydrochloride

4-Amino-3-pyridinol N,N-diethylcarbamate (6.40 g) was dissolved in 100 ml $CH_2Cl_2$ to which $Et_3N$ (3.33 g) had been added. Butanoyl chloride (3.52 g) was then added dropwise and the readtion mixture was stirred 30 minutes. At the end of this time the volatiles were evaporated under reduced pressure and the residue was applied directly to a flash column, eluting with 5% $Et_3N/EtOAc$. Concentration of the product-containing fractions gave 7.43 g of butyramide, which was used without further purification.

The butyramide obtained in this way was dissolved in 60 ml of dry THF and 2.0M $BH_3(CH_3)_2S$ (33 ml) was added. The reaction mixture was refluxed for 30 minutes and then 10 ml of MeOH was added. After the reaction with the residual dibroane had subsided, the solvents were removed under reduced pressure and the residue was re-dissolved in 50 ml of MeOH. This solution was made strongly acidic with $HClEt_2O$ and then refluxed for 1 hour. At the end of this time, the solvents were again removed under reduced pressure and anhydrous hydrazine (25 ml) was added. This mixture was warmed at 80° C. for 30 minutes and then concentrated under reduced pressure, giving a residue which was purified by flash chromatography (10% $MeOH/CH_2Cl_2$, then 20% $MeOH/CH_2Cl_2$). After the product-containing fractions were concentrated, the free base was taken up in a minimum of EtOH and the hydrochloride was formed with $HCl/Et_2O$. Recrystallization from $EtOH/Et_2O$ gave 2.42 g of analytically pure material, m.p. 175°–177° C.
ANALYSIS:
Calculated for $C_9H_{14}N_2O.HCl$: 53.33% C 7.46% H 13.82% N; Found: 53.24% C 7.44% H 13.71 % N

EXAMPLE 36

4-[[(Dihexylamino)methylene]amino]-3-pyridinol N,N-dimethyl carbamate maleate

To a stirred mixture of 4-[[(dihexylamino)methylene]amino]-3-pyridinol (3.30 g) and triethylamine (2.3 ml) in 75 ml dry $Et_2O$ was added dimethyl carbamyl chloride (1.2 ml). The mixture was stirred at room temperature for 18 hours, after which no starting material remained as seen by TLC (silica, 10:90 $CH_3OH:CH_2Cl_2$). The mixture was diluted with $Et_2O$, filtered, and the filtrate concentrated in vacuo and chromatographed on silica using EtOAc eluent. The fractions containing desired product were combined and concentrated to an oil. The maleate salt was prepared in isopropanol, concentrated to dryness, and recrystallized from $CH_2Cl_2/Et_2O$/hexane to provide 2.43 g of the product as a white solid, m.p. 123°–125° C.
ANALYSIS:
Calculated for $C_{25}H_{40}N_4O_6$: 60.96% C 8.18% H 11.37% N; Found: 60.84% C 8.23% H 11.36% N

EXAMPLE 37

4-[[(Diisopropylamino)methylene]amino]-3-pyridinol N,N-dimethyl carbamate

To a stirred mixture of 4-[[(diisopropylamino)methylene] amino]-3-pyridinol (1.06 g) and triethylamine (1.0 ml) in 25 ml dry $Et_2O$ was added dimethyl carbamyl chloride (0.53 ml). The mixture was stirred at room temperature for 2 hours, after which no starting material remained as seen by TLC (silica, 10:90 $CH_3OH:CH_2Cl_2$). The mixture was diluted with 25 ml $Et_2O$, filtered, washed with $Et_2O$, and the filtrate concentrated in vacuo and chromatography on silica using EtOAc eluent. The fractions containing desired product were combined and concentrated to provide 500 mg of pure product. Another run was carried out in the same manner as above using 740 mg of starting material. The products from both runs were combined. Recrystallization attempts failed, and the product was dried in vacuo to provide 790 mg of a white solid, m.p. 76°–79° C.
ANALYSIS:
Calculated for $C_{15}H_{24}N_4O_2$: 61.62% C 8.27% H 19.16% N; Found: 61.63% C 8.27% H 18.82% N

EXAMPLE 38

4-[[(N-methyl-N-butylamino)methylene]amino]-3-pyridinyl-N,N-dimethyl carbamate maleate To a stirred solution of 4-[[(N-methyl-N-butylamino)methylene]amino]-3-pyridinol (2.88 g), triethylamine (2.11 g), and tetrahydrofuran (40 mL) under nitrogen was added N,N-dimethylcarbamyl chloride (1.99 g). The reaction mixture was stirred at ambient temperature for 17 hours, diluted with ether (25 mL), and filtered. The filtrate was concentrated under reduced pressure and the residue chromatographed on silica gel (elution with 10% methanol in dichloromethane) to give 2.41 g of an amber liquid. The liquid was dissolved in isopropanol (25 ml) and a solution of maleic acid (1.00 g) in isopropanol (15 mL) was added. The resulting solution was concentrated under reduced pressure to give a beige solid. Recrystallization from dichloromethane/ethyl acetate afforded 1.37 g (25.0% ) of a white powder, m.p. 130°–133° C.
ANALYSIS:
Calculated for $C_{18}H_{26}N_4O_6$: 54.81% C 6.64% H 14.20% N; Found: 54.87% C 6.60% H 13.97% N

EXAMPLE 39

4-[[(N-methyl-N-cyclohexylamino)methylene] amino]-3-pyridinol N,N-dimethyl carbamate maleate To a solution of 4-[[(N-methyl-N-cyclohexylamino) methylene]amino]-3-pyridinol (2.33 g), triethylamine (1.74 g) and tetrahydrofuran (30 mL) under nitrogen was added N,N-dimethylcarbamyl chloride (1.40 g). The reaction mixture was stirred at ambient temperature for 24 hours, diluted with ether (20 mL) and filtered. The filtrate was concentrated under reduced pressure and the residue chromatographed on silica gel (elution with 10% methanol in dichloromethane) to give 2.25 g of an amber liquid. The liquid was dissolved in isopropanol (20 ml) and a solution of maleic acid (0.866 g) in isopropanol (15 mL) was added. The resulting solution was concentrated under reduced pressure to give a beige solid. Recrystallization from dichloromethane/ethyl acetate afforded 2.37 g of a white crystalline solid, m.p. 157°–159° C.
ANALYSIS:
Calculated for $C_{20}H_{28}N_4O_6$: 57.13% C 6.71% H 13.32% N; Found: 57.40% C 6.75% H 13.34% N

EXAMPLE 40

4-[[(N-Benzyl-N-methylamino)methylene]amino]-3-pyridinol N,N-dimethylcarbamate sesquifumarate 4-[[(Dimethylamino)methylene]amino]-3-pyridinol (3.0 g) was refluxed in N-benzyl-N-methylamine (6.12 ml) and dry toluene (60 ml) overnight. The reaction mixture was concentrated, adhered to silica (MeOH), flash chromatographed (10% MeOH/EtOAc) and concentrated to give 4.4 g of 4-[[(N-benzyl-N-methylamino) methylene]amino]-3-pyridinol.

3.93 g of the pyridinol was refluxed with triethylamine (3.52 ml), dimethylcarbamyl chloride (2.25 ml) and THF (100 ml) for one hour. The reaction mixture was poured directly onto a silica column and eluted successively with EtOAc and 5% Et₃N/EtOAc, and the eluate was concentrated to obtain 4.36 g of an oil.

The oil (4.02 g) was dissolved in 25 ml of boiling ethyl acetate, and a solution of fumaric acid (1.64 g) in 20 ml of methanol was added, followed by the addition of 5 ml of pentane. 2.99 g of the sesquifumarate was collected as a white solid, m.p. 146°–147° C.
ANALYSIS:
Calculated for $C_{17}H_{20}N_4O_2 \cdot C_6H_6O_6$: 56.78% C 5.39% H 11.52% N; Found: 56.80% C 5.44% H 11.18% N

EXAMPLE 41

4-[[(4-Thiomorpholinyl)methylene]amino]-3-pyridinol N,N-dimethylcarbamate

A mixture of 4-[[(4-thiomorpholinyl)methylene]amino]-3-pyridinol (3.28 g), triethylamine (3.17 ml) and dimethylcarbamyl chloride (2.03 ml) in THF (100 ml) was refluxed for 1.25 hours, cooled, poured directly onto a silica column and eluted successively with EtOAC and 5% Et₃N/EtOAc. The eluate was concentrated and triturated with diethyl ether. Recrystallization from ethyl acetate and drying under high vacuum and refluxing ethanol overnight yielded 2.92 g of white needles, m.p. 155.5°–156° C.
Analysis:
Calculated for $C_{13}H_{18}N_4O_2S$: 53.04% C 6.16% H 19.03% N; Found: 52.93% C 6.21% H 18.84% N

We claim:
1. A compound with the formula:

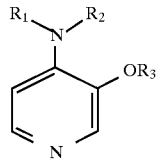

where the group

as a whole is

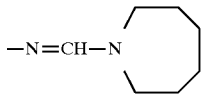

and $R_3$ is hydrogen,

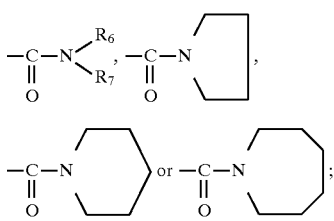

wherein $R_6$ is hydrogen, loweralkyl or phenyl, and $R_7$ is hydrogen or loweralkyl or a pharmaceutically acceptable acid addition salt thereof.

2. The compound as defined in claim 1, which is 4-[[(hexahydro-1H-azepin-1-yl)methylene]amino]-3-pyridinol.

3. The compound as defined in claim 1, which is 4-[[(hexahydro-azepin-1-yl) methylene]amino]-3-pyridinol N,N-dimethylcarbamate.

4. A pharmaceutical composition which comprises a compound as defined in claim 1 in an amount effective for alleviating a memory dysfunction characterized by a cholinergic deficit, and a suitable carrier therefor.

5. A method of treating a patient in need of relief from a memory dysfunction characterized by a cholinergic deficit, which comprises administering to such a patient an effective amount of a compound as defined in claim 1.

* * * * *